(12) United States Patent
Wolf et al.

(10) Patent No.: US 8,815,905 B2
(45) Date of Patent: Aug. 26, 2014

(54) PROPIONIC ACIDS, PROPIONIC ACID ESTERS, AND RELATED COMPOUNDS

(75) Inventors: Mark A. Wolf, Delanson, NY (US); Keith D. Barnes, Rexford, NY (US)

(73) Assignee: Promentis Pharmaceuticals, Inc., Milwaukee, WI (US)

( * ) Notice: Subject to any disclaimer, the term of this patent is extended or adjusted under 35 U.S.C. 154(b) by 38 days.

(21) Appl. No.: 13/042,657

(22) Filed: Mar. 8, 2011

(65) Prior Publication Data

US 2011/0224156 A1 Sep. 15, 2011

Related U.S. Application Data

(60) Provisional application No. 61/312,625, filed on Mar. 10, 2010.

(51) Int. Cl.
| | |
|---|---|
| A61K 31/4406 | (2006.01) |
| A61P 25/18 | (2006.01) |
| A61P 25/30 | (2006.01) |
| C07D 211/80 | (2006.01) |
| C07D 401/12 | (2006.01) |
| C07D 403/12 | (2006.01) |
| C07C 323/52 | (2006.01) |
| C07C 327/34 | (2006.01) |
| C07C 271/20 | (2006.01) |
| C07D 241/08 | (2006.01) |
| C07D 213/56 | (2006.01) |
| C07D 413/12 | (2006.01) |
| C07D 277/06 | (2006.01) |
| A61K 31/7024 | (2006.01) |
| A61K 31/198 | (2006.01) |
| A61K 31/422 | (2006.01) |
| A61K 31/426 | (2006.01) |

(52) U.S. Cl.
USPC ............ 514/316; 514/355; 546/262; 546/316

(58) Field of Classification Search
None
See application file for complete search history.

(56) References Cited

U.S. PATENT DOCUMENTS

| | | | | |
|---|---|---|---|---|
| 6,623,723 | B2 * | 9/2003 | Katz | 424/46 |
| 7,227,028 | B2 * | 6/2007 | Gallop et al. | 548/542 |
| 8,173,809 | B2 * | 5/2012 | Cook et al. | 544/385 |
| 2008/0051458 | A1 * | 2/2008 | Dai et al. | 514/563 |

OTHER PUBLICATIONS

Park, H. et al "Selective reduction of trigonellyl group . . . " Bull. Korean Chem. Soc. (2008) vo 29, No. 2, pp. 479-482.*
Rautio, J. et al "Prodrug approaches for CNS delivery" AAPS J. (2008) vol. 10, No. 1, pp. 92-102.*
Caplus entry for Katz (US 2003/0039615), Document number: 138:726 (2012).*

* cited by examiner

*Primary Examiner* — Leigh Maier
(74) *Attorney, Agent, or Firm* — Wood, Phillips, Katz, Clark & Mortimer

(57) ABSTRACT

The invention relates to propionic acids, propionic acid esters, and related compounds, pharmaceutical compositions containing these compounds, and methods of using these compounds for the treatment of various diseases or conditions, including but not limited to diseases and/or conditions of Central Nervous System (CNS).

5 Claims, No Drawings

PROPIONIC ACIDS, PROPIONIC ACID ESTERS, AND RELATED COMPOUNDS

FIELD OF THE INVENTION

This invention relates to novel propionic acids, propionic acid esters, and related compounds and methods of using these compounds for the treatment of diseases and/or conditions, including but not limited to diseases and/or conditions of Central Nervous System (CNS), including schizophrenia and drug addiction.

BACKGROUND OF THE INVENTION

Schizophrenia is a debilitating disorder afflicting 1% of the world's population. The development of effective medications to treat schizophrenia relies on advances in characterizing the underlying pathophysiology. Chlorpromazine and other phenothiazines are considered first generation antipsychotics (termed "typical antipsychotics") useful in the treatment of schizophrenia.

Schizophrenia may be associated with diminished signaling to glutamate receptors and diminished glutathione levels. A depleted glutathione level can lead to increased oxidative stress, and impaired cystine-glutamate antiporter activity, glutamate neurotransmission, synaptic connection, and gene expression, all of which are observed in schizophrenia. In addition, impaired cystine-glutamate antiporter activity and faulty glutamate neurotransmission bear on the issue of uncontrolled drug use, i.e., drug addiction.

Cysteine prodrugs, such as N-acetylcysteine ("NAC"), are used to drive cystine-glutamate exchange by apparently elevating extracellular cystine levels, thereby creating a steep cystine concentration gradient.

However, alternatives to NAC are needed. NAC undergoes extensive first pass metabolism requiring the usage of high doses that limit the utility of the drug and, potentially, increase the chances of side effects due to the buildup of metabolized by-products. The compounds of the present invention are designed to substantially avoid the problem of first pass metabolism and therefore exhibit increased efficacy as compared to NAC and other prior cysteine prodrugs.

Accordingly, there is a need for novel compounds that would have a reduced incidence of problems associated with NAC.

SUMMARY OF THE INVENTION

In one aspect, the present invention is directed to compounds of formula I:

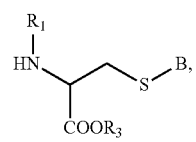

where
B is selected from the group consisting of:

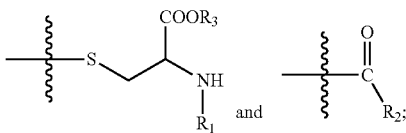

$R_1$ is selected from the group consisting of

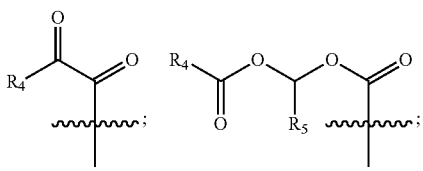

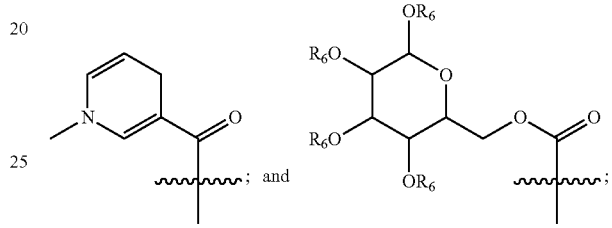

$R_2$ is a linear or branched $C_1$-$C_6$ alkyl;
$R_3$ is selected from the group consisting of H and a linear or branched $C_1$-$C_6$ alkyl;
$R_4$ and $R_5$ are independently a linear or branched $C_1$-$C_6$ alkyl; and
$R_6$ is H or

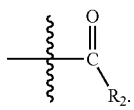

In another aspect, the present invention is directed to compounds of formula II:

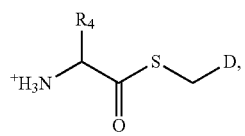

where
D is

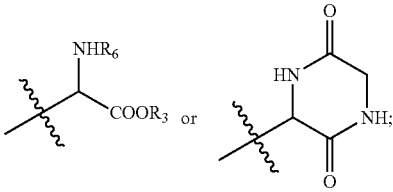

$R_3$ is selected from the group consisting of H and linear or branched $C_1$-$C_6$ alkyl;

$R_4$ is a linear or branched $C_1$-$C_6$ alkyl;
$R_6$ is selected from the group consisting of H and

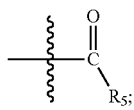

and
$R_5$ is a linear or branched $C_1$-$C_6$ alkyl.

In another aspect, the present invention is directed to compounds of formula III:

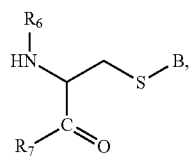

III where B is selected from the group consisting of

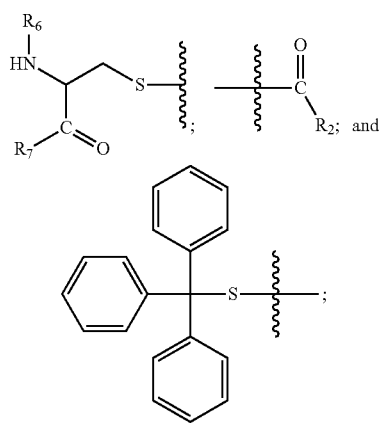

$R_7$ is selected from the group consisting of

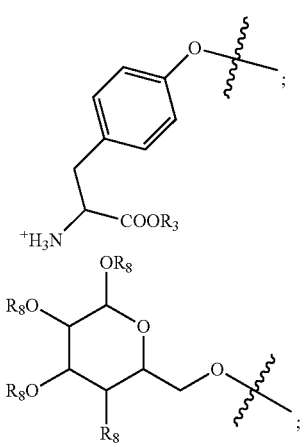

and —S—CH$_2$F;
$R_2$ is a linear or branched $C_1$-$C_6$ alkyl;
$R_3$ is selected from the group consisting of H and linear or branched $C_1$-$C_6$ alkyl; and $R_6$ and $R_8$ are independently selected from the group consisting of H and

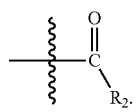

In yet another aspect, the present invention is directed to compounds of formula IV:

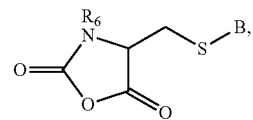

IV where
B is selected from the group consisting of:

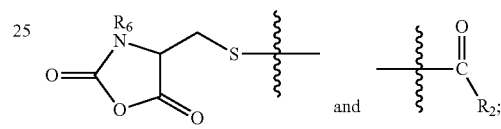

$R_2$ is selected from the group consisting of a linear or branched $C_1$-$C_6$ alkyl; and
$R_6$ is selected from the group consisting of H and

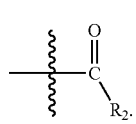

In yet another aspect, the present invention is directed to compounds of formula V:

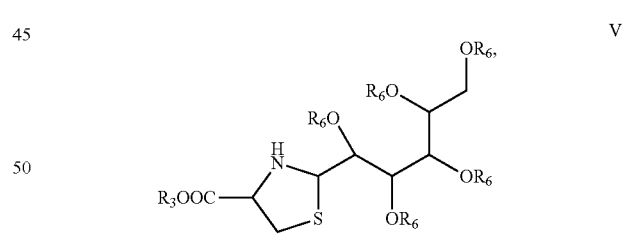

V where $R_3$ is selected from the group consisting of H and a linear or branched $C_1$-$C_6$ alkyl;
$R_6$ is selected from the group consisting of H and

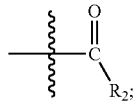

and
$R_2$ is selected from the group consisting of a linear or branched $C_1$-$C_6$ alkyl.

The invention also encompasses pharmaceutically acceptable salts of the provided compounds.

In another aspect, the invention is directed to a method of treating a disease or condition in a subject comprising administering to the subject a therapeutically effective amount of a compound of any of Formulas I-V or a pharmaceutically acceptable salt thereof. The preferred route of administering to the subject is via oral delivery. Preferably, diseases or conditions treatable with the compounds of the present invention are related to central nervous system (CNS).

In a preferred embodiment, the disease is schizophrenia.

In another aspect, the invention provides a method of treating drug craving in a subject comprising administering to the subject a therapeutically effective amount of a compound of any of Formulas I-V or a pharmaceutically acceptable salt thereof. The preferred route of administering to the subject is via oral delivery.

The invention further encompasses pharmaceutical compositions containing a compound of any of Formulas I-V or a pharmaceutically acceptable salt thereof in combination with a pharmaceutically-acceptable carrier.

Methods of formulating/manufacturing such pharmaceutical compositions (alternatively termed "medicaments") for the treatment of a disease or condition in a subject are also within the invention's scope.

DETAILED DESCRIPTION OF THE INVENTION

The following definitions are used, unless otherwise described.

The term "lower alkyl group(s)" as used herein indicates a linear, branched or cyclic alkyl groups having I to 6 carbon atoms. They include, for example, methyl group, ethyl group, n-propyl group, n-butyl group, n-pentyl group, n-hexyl group, isopropyl group, isobutyl group, sec-butyl group, tert-butyl group, isopentyl group, tert-pentyl group, neopentyl group, 2-pentyl group, 3-pentyl group, 3-hexyl group, 2-hexyl group, cyclopropyl group, cyclobutyl group, cyclopentyl group and cyclohexyl group. In them, methyl group, ethyl group, etc. are preferred.

The term "aryl group(s)" as used herein indicates a mono-cyclic or bicyclic aromatic substituent(s) composed of 5 to 12 carbon atoms, such as phenyl group, indenyl group, naphthyl group and fluorenyl group. In them, phenyl group is preferred. An aryl group can be substituted. The term "arylthio group" indicates a mono cyclic or bicyclic aromatic substituent(s) composed of 5 to 12 carbon atoms and further including a thio moiety.

The term "alkoxy group" refers to an alkyl (carbon and hydrogen chain) group linked to oxygen thus: R—O.

The term "aryloxy group" refers to an aryl group linked to oxygen thus: Ar-O.

The term "acyl group(s)" as used herein indicates a formyl group, an acyl group(s) having a linear, branched or cyclic alkyl group having 1 to 6 carbon atoms, acyl group (s) having a linear, branched or cyclic alkenyl group having 1 to 6 carbon atoms, acyl group(s) having a linear, branched or cyclic alkynyl group having 1 to 6 carbon atoms or acyl group(s) having an aryl group which may be substituted, such as formyl group, acetyl group, propionyl group, butyryl group, isobutyryl group, valeryl group, isovaleryl group, pivaloyl group, hexanoyl group, acryloyl group, methacryloyl group, crotonoyl group, isocrotonoyl group, benzoyl group and naphthoyl group. Acyl groups having a heterocyclic ring can also be used, for example, furanyl carbonyl group, thienyl carbonyl group, isoxazolyl carbonyl group and thiazolyl carbonyl group.

In general, unless indicated otherwise, a chemical group referred to anywhere in the specification can be optionally substituted.

The term "prodrugs" refers to compounds, including monomers and dimers of the compounds of the invention, which have cleavable groups and become under physiological conditions compounds which are pharmaceutically active in vivo.

The term "dimer" refers to the chemical entity formed by disulfide linkage of two identical prodrugs, or protected cysteine analogs described herein.

The term "subject" includes humans. The terms "human," "patient" and "subject" are used interchangeably.

The term "sugar" refers to any mono- and disaccharides and specifically includes, but is not limited to, acid esters of sugars. For example, a sugar can be substituted with OAc group(s) at any carbons in the sugar ring.

The term "therapeutically effective amount" means the amount of a compound that, when administered to a subject for treating a disease or disorder, is sufficient to effect such treatment for the disease or disorder. The "therapeutically effective amount" can vary depending on the compound, the disease or disorder and its severity, and the age, weight, etc., of the subject to be treated.

The terms "treating" or "treatment" of any disease or disorder refer, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder, or even preventing the same.

In one aspect, the present invention is directed to compounds of formula I:

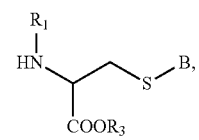

where

B is selected from the group consisting of:

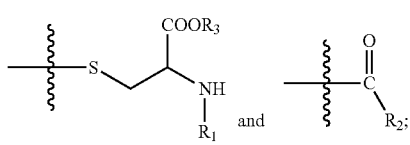

$R_1$ is selected from the group consisting of

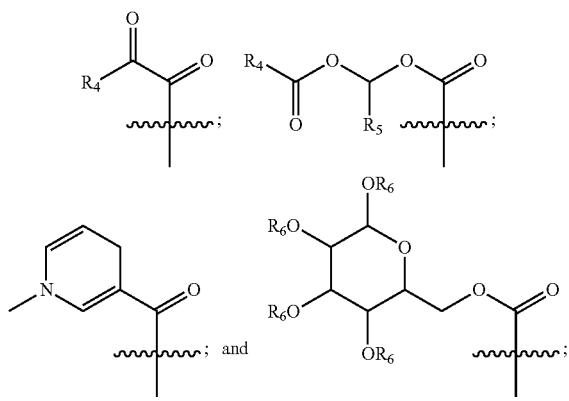

$R_2$ is a linear or branched $C_1$-$C_6$ alkyl;
$R_3$ is selected from the group consisting of H and a linear or branched $C_1$-$C_6$ alkyl;
$R_4$ and $R_6$ are independently a linear or branched $C_1$-$C_6$ alkyl; and
$R_6$ is H or

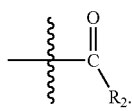

In another aspect, the present invention is directed to compounds of formula II:

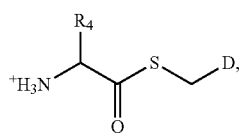

where
D is

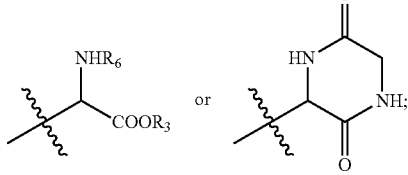

$R_3$ is selected from the group consisting of H and linear or branched $C_1$-$C_6$ alkyl;
$R_4$ is a linear or branched $C_1$-$C_6$ alkyl;
$R_6$ is selected from the group consisting of H and

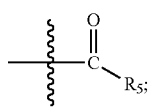

and
$R_5$ is a linear or branched $C_1$-$C_6$ alkyl.

In another aspect, the present invention is directed to compounds of formula III:

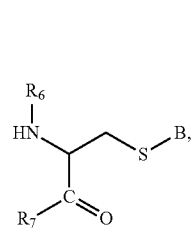

where B is selected from the group consisting of

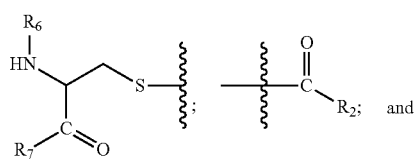

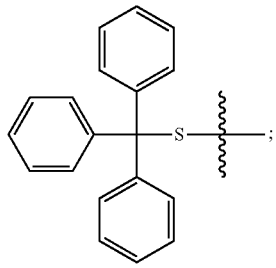

$R_7$ is selected from the group consisting of

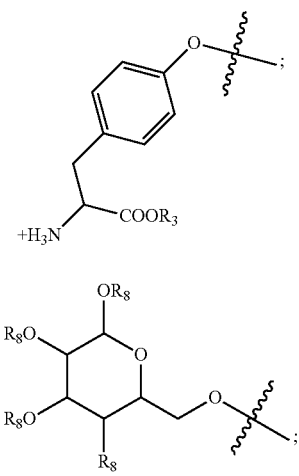

and —S—CH$_2$F;
$R_2$ is a linear or branched $C_1$-$C_6$ alkyl;
$R_3$ is selected from the group consisting of H and linear or branched $C_1$-$C_6$ alkyl; and
$R_6$ and $R_8$ are independently selected from the group consisting of H and

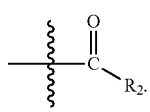

In yet another aspect, the present invention is directed to compounds of formula IV:

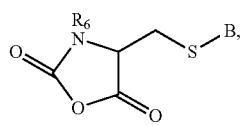

where
B is selected from the group consisting of:

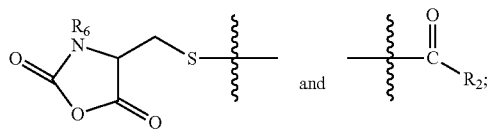

$R_2$ is selected from the group consisting of a linear or branched $C_1$-$C_6$ alkyl; and
$R_6$ is selected from the group consisting of H and

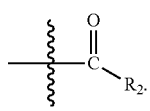

In yet another aspect, the present invention is directed to compounds of formula V:

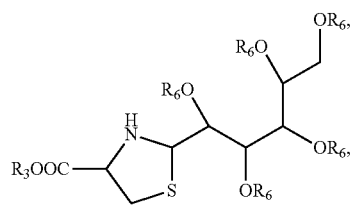

where $R_3$ is selected from the group consisting of H and a linear or branched $C_1$-$C_6$ alkyl;
$R_6$ is selected from the group consisting of H and

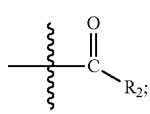

and
$R_2$ is selected from the group consisting of a linear or branched $C_1$-$C_6$ alkyl.

Presently Preferred Compounds Include:

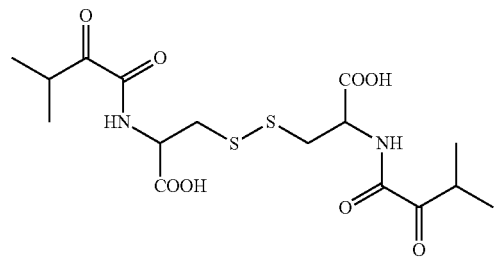 [SMILES: CC(C)C(=O)C(=O)NC(CSSCC(NC(=O)C(=O)C(C)C)C(=O)O)C(=O)O]

3-[2-Carboxy-2-(3-methyl-2-oxo-butyrylamino)-ethyldisulfanyl]-2-(3-methyl-2-oxo-butyrylamino)-propionic acid

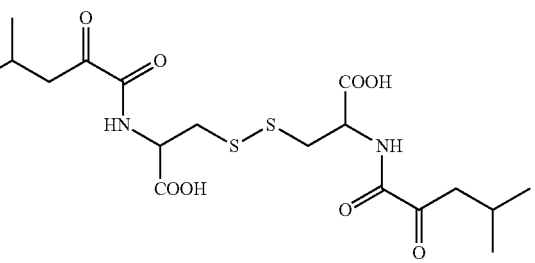

3-[2-Carboxy-2-(4-methyl-2-oxo-pentanoylamino)-ethyldisulfanyl]-2-(4-methyl-2-oxo-pentanoy-lamino)-propionic acid

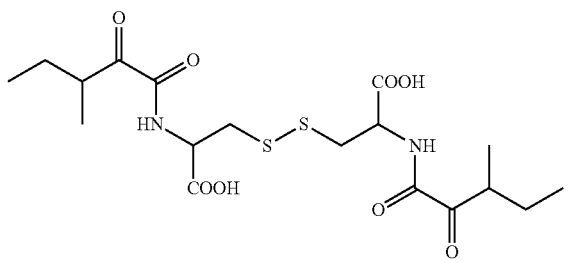 [SMILES: CCC(C)C(=O)C(=O)NC(CSSCC(NC(=O)C(=O)C(C)CC)C(=O)O)C(=O)O]

3-[2-Carboxy-2-(3-methyl-2-oxo-pentanoylamino)-ethyldisulfanyl]-2-(3-methyl-2-oxo-pentanoy-lamino)-propionic acid

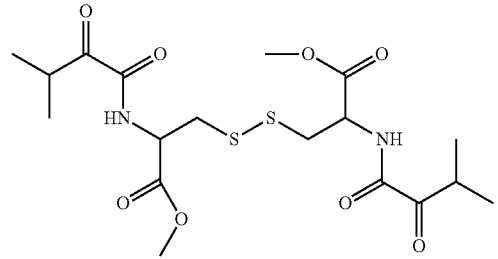 [SMILES: COC(=O)C(CSSCC(NC(=O)C(=O)C(C)C)C(=O)OC)NC(=O)C(=O)C(C)C]

11

3-[2-Methoxycarbonyl-2-(3-methyl-2-oxo-butyrylamino)-ethyldisulfanyl]-2-(3-methyl-2-oxo-butyrylamino)-propionic acid methyl ester

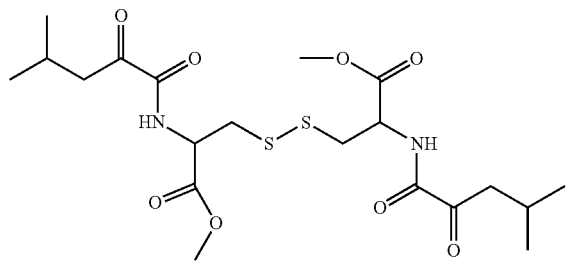 [SMILES: COC(=O)C(CSSCC(NC(=O)C(=O)CC(C)C)C(=O)OC)NC(=O)C(=O)CC(C)C]

3-[2-Methoxycarbonyl-2-(4-methyl-2-oxo-pentanoylamino)-ethyldisulfanyl]-2-(4-methyl-2-oxo-pentanoylamino)-propionic acid methyl ester

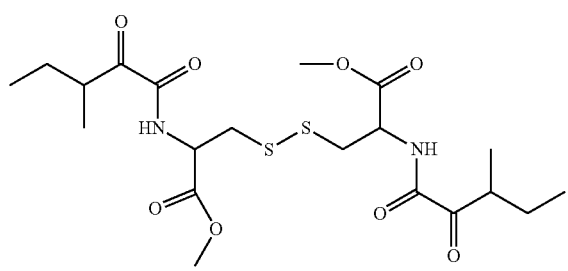 [SMILES: CCC(C)C(=O)C(=O)NC(CSSCC(NC(=O)C(=O)C(C)CC)C(=O)OC)C(=O)OC]

3-[2-Methoxycarbonyl-2-(3-methyl-2-oxo-pentanoylamino)-ethyldisulfanyl]-2-(3-methyl-2-oxo-pentanoylamino)-propionic acid methyl ester

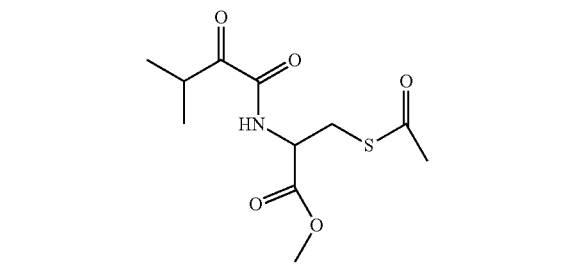 [SMILES: COC(=O)C(CSC(C)=O)NC(=O)C(=O)C(C)C]

3-Acetylsulfanyl-2-(3-methyl-2-oxo-butyrylamino)-propionic acid methyl ester

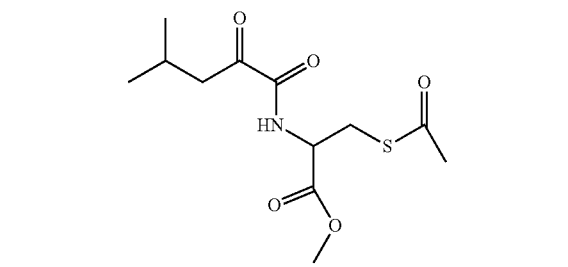 [SMILES: COC(=O)C(CSC(C)=O)NC(=O)C(=O)CC(C)C]

12

3-Acetylsulfanyl-2-(4-methyl-2-oxo-pentanoylamino)-propionic acid methyl ester

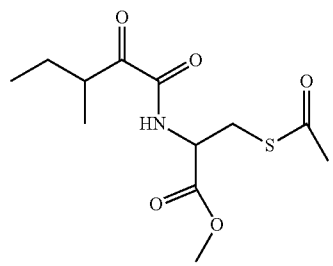 [SMILES: CCC(C)C(=O)C(=O)NC(CSC(C)=O)C(=O)OC]

3-Acetylsulfanyl-2-(3-methyl-2-oxo-pentanoylamino)-propionic acid methyl ester

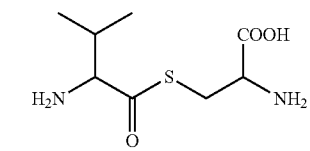

2-Amino-3-(2-amino-3-methyl-butyrylsulfanyl)-propionic acid

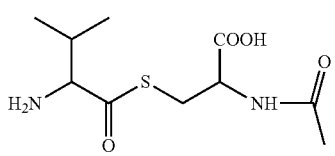

2-Acetylamino-3-(2-amino-3-methyl-butyrylsulfanyl)-propionic acid

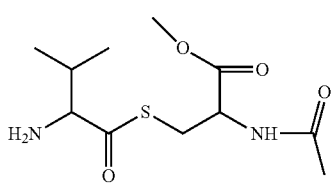

2-Acetylamino-3-(2-amino-3-methyl-butyrylsulfanyl)-propionic acid methyl ester

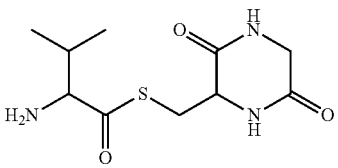 [SMILES: CC(C)C(N)C(=O)SCC1NC(=O)CNC1=O]

2-Amino-3-methyl-thiobutyric acid S-(3,6-dioxo-piperazin-2-ylmethyl)ester

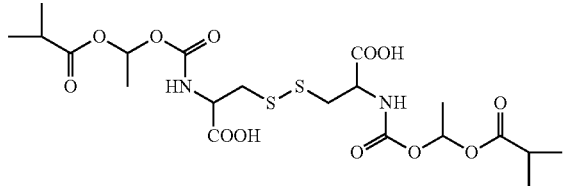 [SMILES: CC(OC(=O)NC(CSSCC(NC(=O)OC(C)OC(=O)C(C)C)C(=O)O)C(=O)O)OC(=O)C(C)C]

3-[2-Carboxy-2-(1-isobutyryloxy-ethoxycarbony-lamino)-ethyldisulfanyl]-2-(1-isobutyryloxy-ethoxy-carbonylamino)-propionic acid

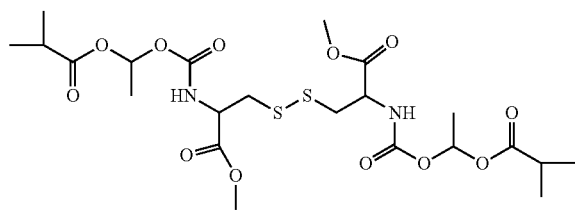 [SMILES: COC(=O)C(CSSCC(NC(=O)OC(C)OC(=O)C(C)C)C(=O)OC)NC(=O)OC(C)OC(=O)C(C)C]

2-(1-Isobutyryloxy-ethoxycarbonylamino)-3-[2-(1-isobutyryloxy-ethoxycarbonylamino)-2-methoxycar-bonyl-ethyldisulfanyl]-propionic acid methyl ester

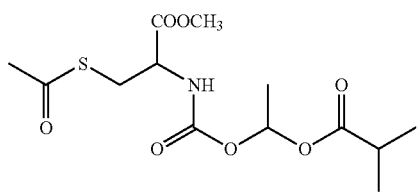 [SMILES: COC(=O)C(CSC(C)=O)NC(=O)OC(C)OC(=O)C(C)C]

3-Acetylsulfanyl-2-(1-isobutyryloxy-ethoxycarbony-lamino)-propionic acid methyl ester

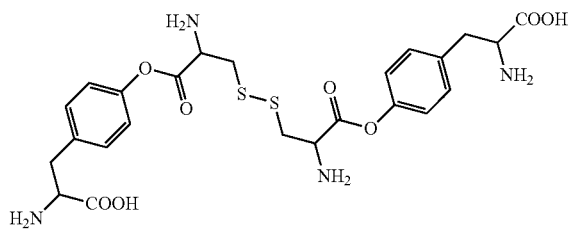 [SMILES: NC(Cc1ccc(OC(=O)C(N)CSSCC(N)C(=O)Oc2ccc(CC(N)C(=O)O)cc2)cc1)C(=O)O]

2-Amino-3-[4-(2-amino-3-{2-amino-2-[4-(2-amino-2-carboxy-ethyl)-phenoxycarbonyl]-ethyldisulfa-nyl}-propionyloxy)-phenyl]-propionic acid

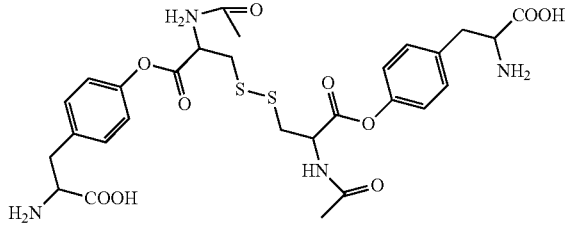 [SMILES: CC(=O)NC(CSSCC(NC(C)=O)C(=O)Oc1ccc(CC(N)C(=O)O)cc1)C(=O)Oc1ccc(CC(N)C(=O)O)cc1]

3-[4-(2-Acetylamino-3-{2-acetylamino-2-[4-(2-amino-2-carboxy-ethyl)-phenoxycarbonyl]-ethyldis-ulfanyl}-propionyloxy)-phenyl]-2-amino-propionic acid

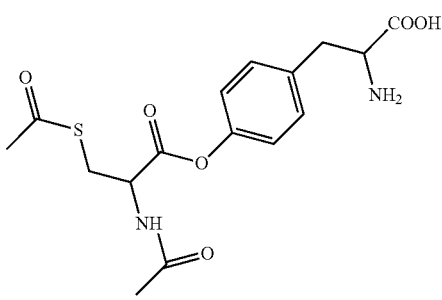 [SMILES: CC(=O)NC(CSC(C)=O)C(=O)Oc1ccc(CC(N)C(=O)O)cc1]

3-[4-(2-Acetylamino-3-acetylsulfanyl-propiony-loxy)-phenyl]-2-amino-propionic acid

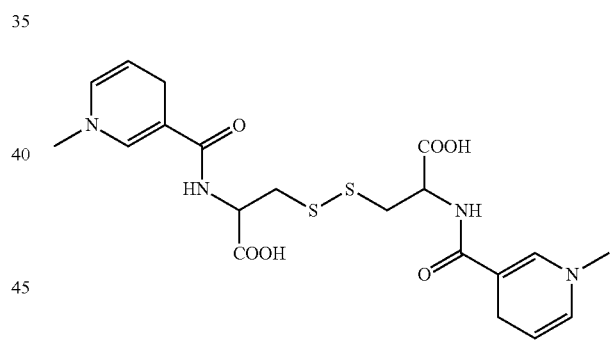

3-{2-Carboxy-2-[(1-methyl-1,4-dihydro-pyridine-3-carbonyl)-amino]-ethyldisulfanyl}-2-[(1-methyl-1,4-dihydro-pyridine-3-carbonyl)-amino]-propionic acid

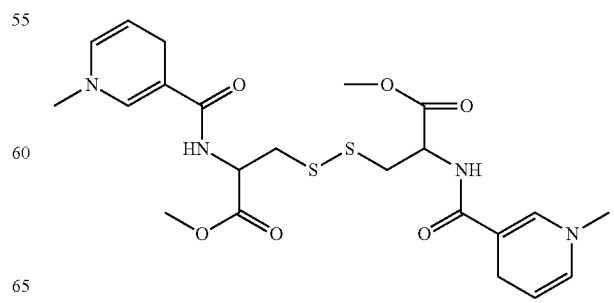

15

3-{2-Methoxycarbonyl-2-[(1-methyl-1,4-dihydro-pyridine-3-carbonyl)-amino]-ethyldisulfanyl}-2-[(1-methyl-1,4-dihydro-pyridine-3-carbonyl)-amino]-propionic acid methyl ester

16

2-Acetylamino-3-[2-acetylamine-2-(3,4,5,6-tetrahydroxy-tetrahydro-pyran-2-ylmethoxycarbonyl)-ethyldisulfanyl]-propionic acid 3,4,5,6-tetrahydroxy-tetrahydro-pyran-2-ylmethyl ester

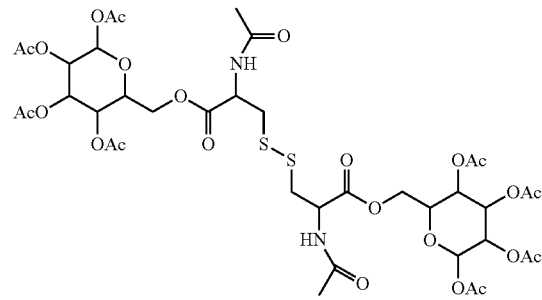

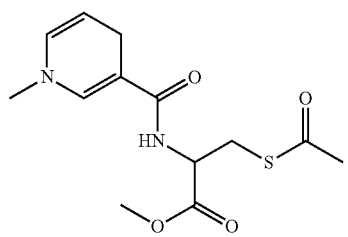 [SMILES: COC(=O)C(CSC(C)=O)NC(=O)C1=CN(C)C=CC1]

2-Acetylamino-3-[2-acetylamino-2-(3,4,5,6-tetraacetoxy-tetrahydro-pyran-2-ylmethoxycarbonyl)-ethyldisulfanyl]-propionic acid 3,4,5,6-tetraacetoxy-tetrahydro-pyran-2-ylmethyl ester 3-Acetylsulfanyl-2-[(1-methyl-1,4-dihydro-pyridine-3-carbonyl)-amino]-propionic acid methyl ester

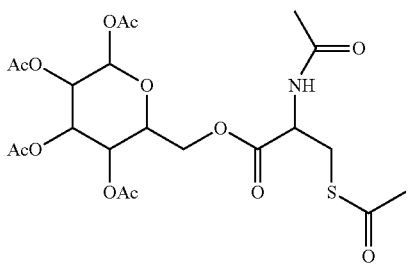

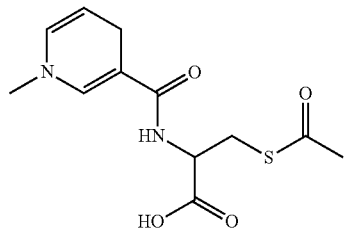 [SMILES: CC(=O)SCC(NC(=O)C1=CN(C)C=CC1)C(=O)O]

2-Acetylamino-3-acetylsulfanyl-propionic acid 3,4,5,6-tetraacetoxy-tetrahydro-pyran-2-ylmethyl ester 3-Acetylsulfanyl-2-[(1-methyl-1,4-dihydro-pyridine-3-carbonyl)-amino]-propionic acid

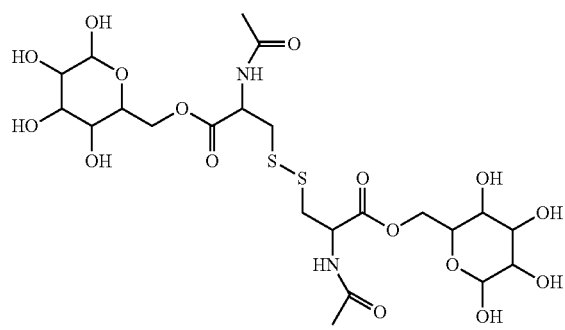 [SMILES: CC(=O)NC(CSSCC(NC(C)=O)C(=O)OCC1OC(O)C(O)C(O)C1O)C(=O)OCC1OC(O)C(O)C(O)C1O]

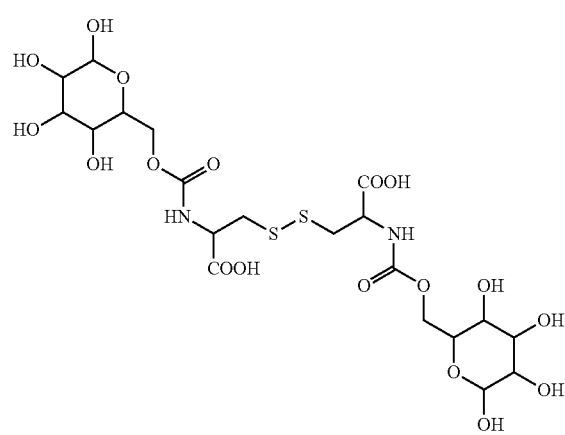 [SMILES: O=C(NC(CSSCC(NC(=O)OCC1OC(O)C(O)C(O)C1O)C(=O)O)C(=O)O)OCC1OC(O)C(O)C(O)C1O]

17

3-[2-Carboxy-2-(3,4,5,6-tetrahydroxy-tetrahydro-pyran-2-ylmethoxycarbonylamino)-ethyldisulfanyl]-2-(3,4,5,6-tetrahydroxy-tetrahydro-pyran-2-yl-methoxycarbonylamino)-propionic acid

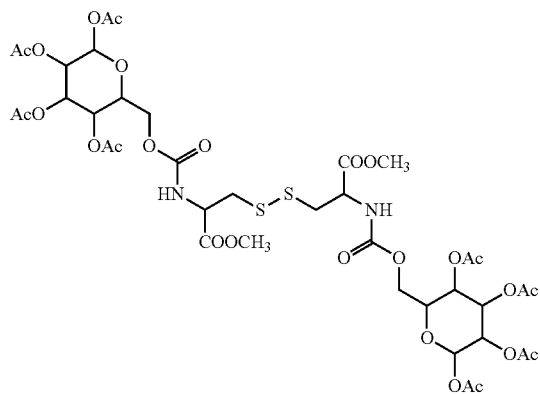 [SMILES: COC(=O)C(CSSCC(NC(=O)OCC1OC(OC(C)=O)C(OC(C)=O)C(OC(C)=O)C1OC(C)=O)C(=O)OC)NC(=O)OCC1OC(OC(C)=O)C(OC(C)=O)C(OC(C)=O)C1OC(C)=O]

3-[2-Methoxycarbonyl-2-(3,4,5,6-tetraacetoxy-tetrahydro-pyran-2-ylmethoxycarbonylamino)-ethyldisulfanyl]-2-(3,4,5,6-tetraacetoxy-tetrahydro-pyran-2-ylmethoxycarbonylamino)-propionic acid methyl ester

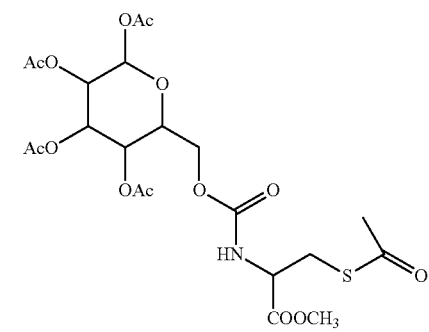 [SMILES: COC(=O)C(CSC(C)=O)NC(=O)OCC1OC(OC(C)=O)C(OC(C)=O)C(OC(C)=O)C1OC(C)=O]

3-Acetylsulfanyl-2-(3,4,5,6-tetraacetoxy-tetrahydro-pyran-2-ylmethoxycarbonylamino)-propionic acid methyl ester

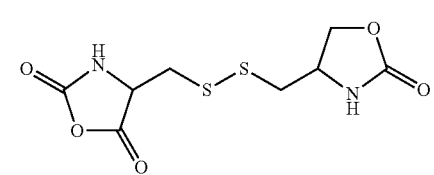 [SMILES: O=C1NC(CSSCC2NC(=O)OC2=O)CO1]

18

4,4'-disulfanediylbis(methylene)dioxazolidine-2,5-dione

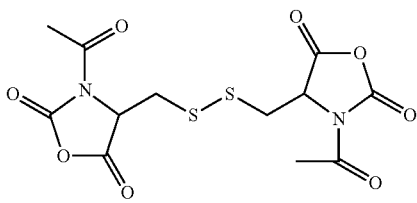 [SMILES: CC(=O)N1C(=O)OC(=O)C1CSSCC1C(=O)OC(=O)N1C(C)=O]

4,4'-disulfanediylbis(methylene)bis(3-acetyloxazolidine-2,5-dione)

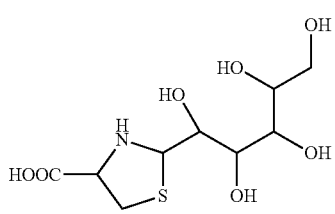 [SMILES: O=C(O)C1CSC(C(O)C(O)C(O)C(O)CO)N1]

2-(1,2,3,4,5-Pentahydroxy-pentyl)-thiazolidine-4-carboxylic acid

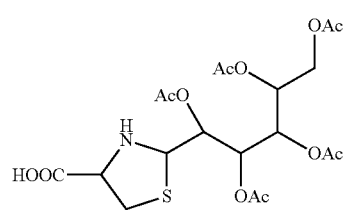 [SMILES: CC(=O)OCC(OC(C)=O)C(OC(C)=O)C(OC(C)=O)C(OC(C)=O)C1NC(C(=O)O)CS1]

2-(1,2,3,4,5-Pentaacetoxy-pentyl)-thiazolidine-4-carboxylic acid

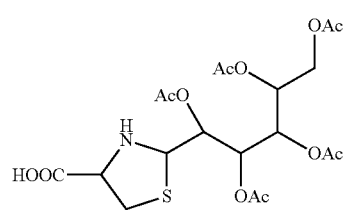 [SMILES: CC(=O)OCC(OC(C)=O)C(OC(C)=O)C(OC(C)=O)C(OC(C)=O)C1NC(C(=O)O)CS1]

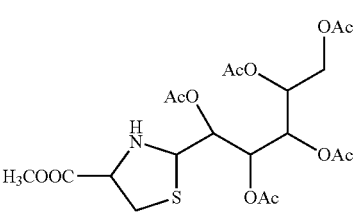

2-(1,2,3,4,5-Pentaacetoxy-pentyl)-thiazolidine-4-carboxylic acid methyl ester

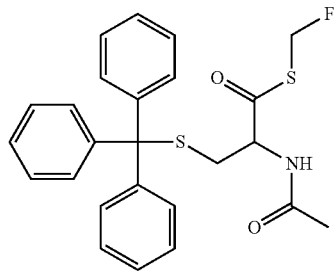 [SMILES: CC(=O)NC(CSC(c1ccccc1)(c1ccccc1)c1ccccc1)C(=O)SCF]

2-Acetylamino-3-tritylsulfanyl-thiopropionic acid S-fluoromethyl ester

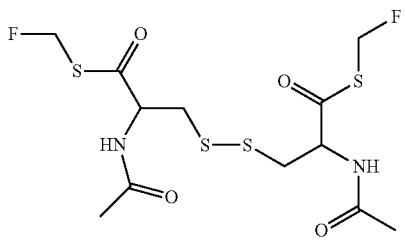 [SMILES: CC(=O)NC(CSSCC(NC(C)=O)C(=O)SCF)C(=O)SCF]

2-Acetylamino-3-(2-acetylamino-2-fluoromethylsulfanylcarbonyl-ethyldisulfanyl)-thiopropionic acid S-fluoromethyl ester; and

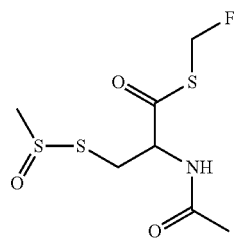

2-Acetylamino-3-acetylsulfanyl-thiopropionic acid S-fluoromethyl ester

Certain compounds of the invention may exist in different isomeric (e.g. enantiomers and distereoisomers) forms. The invention contemplates all such isomers both in pure form and in admixture, including racemic mixtures. Enol forms are also included.

The compounds of the invention can exist in unsolvated as well as solvated forms, including hydrated forms, e.g., hemihydrate. In general, the solvated forms, with pharmaceutically acceptable solvents such as water, ethanol, and the like are equivalent to the unsolvated forms for the purposes of the invention.

Certain compounds of the invention also form pharmaceutically acceptable salts, e.g., acid addition salts. For example, the nitrogen atoms may form salts with acids. Examples of suitable acids for salt formation are hydrochloric, sulfuric, phosphoric, acetic, citric, oxalic, malonic, salicylic, malic, furmaric, succinic, ascorbic, maleic, methanesulfonic and other mineral carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous hydroxide potassium carbonate, ammonia, and sodium bicarbonate. The free base forms differ from their respective salt forms somewhat in certain physical properties, such as solubility in polar solvents, but the acid salts are equivalent to their respective free base forms for purposes of the invention. (See, for example S. M. Berge, et al., "Pharmaceutical Salts," *J. Pharm. Sci.*, 66: 1-19 (1977) which is incorporated herein by reference.)

As used herein, the term "composition" is intended to encompass a product comprising the specified ingredients in the specified amounts, as well as any product which results, directly or indirectly, from a combination of the specified ingredients in the specified amounts.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in *J. Pharmaceutical Sciences*, 1977, 66: 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate(isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients.

The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.0001 to about 1000 mg/kg/day. For purposes of oral administration, more preferable doses can be in the range of from about 0.001 to about 5 mg/kg/day. If desired, the effective daily dose can be divided into multiple doses for purposes of administration; consequently, single dose compositions may contain such amounts or submultiples thereof to make up the daily dose.

The present invention also provides pharmaceutical compositions that comprise compounds of the present invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracisternally, intravaginally, transdermally (e.g. using a patch), transmucosally, sublingually, pulmonary, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

In another aspect, the present invention provides a pharmaceutical composition comprising a component of the present invention and a physiologically tolerable diluent. The present invention includes one or more compounds as described above formulated into compositions together with one or more non-toxic physiologically tolerable or acceptable diluents, carriers, adjuvants or vehicles that are collectively referred to herein as diluents, for parenteral injection, for intranasal delivery, for oral administration in solid or liquid form, for rectal or topical administration, among others.

Compositions suitable for parenteral injection may comprise physiologically acceptable, sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology*, Volume XIV, Academic Press, New York, N.Y. (1976), p. 33 et seq.

In another aspect, the invention is directed to a method of treating a disease or condition in a subject comprising administering to the subject a therapeutically effective amount of a compound of any of Formulas I-V or a pharmaceutically acceptable salt thereof. The preferred route of administering to the subject is via oral delivery.

Preferably, diseases or conditions treatable with the compounds of the present invention are related to central nervous system (CNS). In a preferred embodiment, the disease is schizophrenia.

However, it is within a skill in the art that the provided compounds may be used to treat other diseases or conditions associated with diminished glutathione levels and/or glutamate signaling, and/or oxidative stress, and/or impaired cystine-glutamate antiporter activity, glutamate neurotransmission, synaptic connection, and gene expression.

In general, the invention is not limited to treatment of any specific disease or condition but encompasses the treatment of any disease or condition whose mechanism may be affected by the compounds of the present invention.

In another aspect, the invention provides a method of treating drug craving in a subject comprising administering to the subject a therapeutically effective amount of a compound of any of Formulas I-V or a pharmaceutically acceptable salt thereof. The preferred route of administering to the subject is via oral delivery.

The invention further encompasses pharmaceutical compositions containing a compound of any of Formulas I-V or a pharmaceutically acceptable salt thereof in combination with a pharmaceutically-acceptable carrier.

Methods of formulating/manufacturing such pharmaceutical compositions (alternatively termed "medicaments") for the treatment of a disease or condition in a subject are also within the invention's scope.

For a clearer understanding of the invention, details are provided below. These are merely illustrations and are not to be understood as limiting the scope of the invention in any way. Indeed, various modifications of the invention in addition to those shown and described herein will become apparent to those skilled in the art from the following examples and foregoing description. Such modifications are also intended to fall within the scope of the appended claims.

EXAMPLES

Exemplary synthetic strategies are outlined in Schemes 1-11 which yield cysteine and cystine prodrugs according to the present invention.

Unless indicated otherwise, all R, R', etc substituents of the compounds described in Schemes 1-11 correspond to the substituents of the described and claimed compounds.

Further, while some of the compounds described in Schemes 1-11 may have a positive or negative charge, it is within a skill in the art to arrive at the corresponding neutrally charged compounds which are within the scope of the invention.

No representation has been made that the actual synthesis has been performed; as the described schemes are prophetic. Although, it is believed that a person of skill in the art would know how to synthesize the claimed compounds based, in part, on the provided Schemes 1-11.

hPEPT1 Substrates

Compounds of structure 1 demonstrate improved uptake by virtue of facilitated uptake mediated by the human oligopeptide-1 (hPEPT1) transporter. Conversion of the prodrug in vivo provides elevated levels of cystine to facilitate cystine-glutamate exchange in the central nervous system (CNS). Compounds of structure 1 may be prepared as shown in Scheme 1:

optionally in the presence of a base like triethylamine or the like, in a solvent such as dimethylformamide (DMF) or tetrahydrofuran (THF) or the like.

This intermediate may then be N-acylated with an aliphatic a-ketoacid, preferentially 2-oxovaleric acid, 2-oxo-4-methylvaleric acid, 2-oxo-3-methylvaleric acid or the like, in the presence of an activating agent like water-soluble carbodiimide (WSC) or N,N'-dicyclohexylcarbodiimide/hydroxyben-

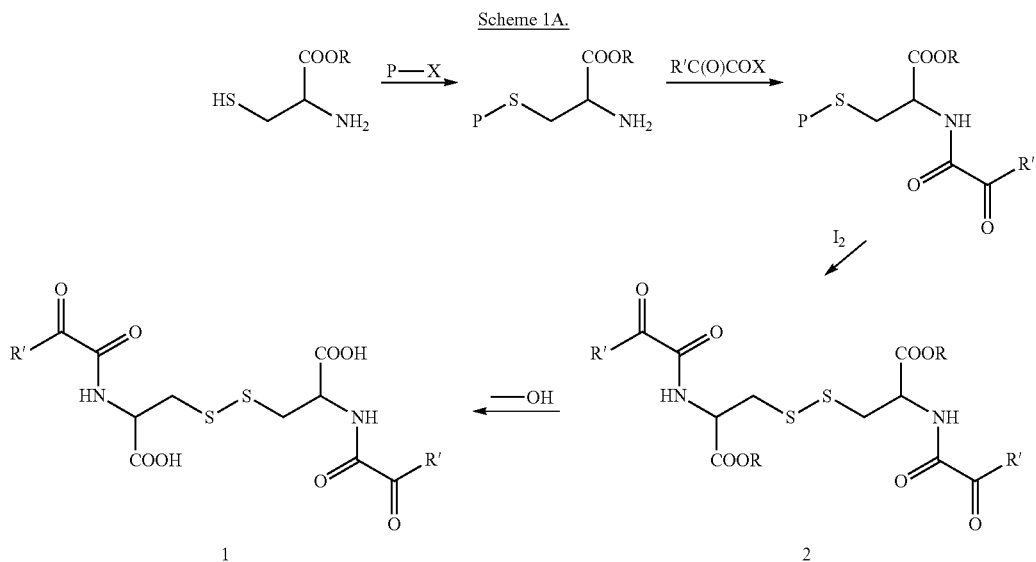

Scheme 1A.

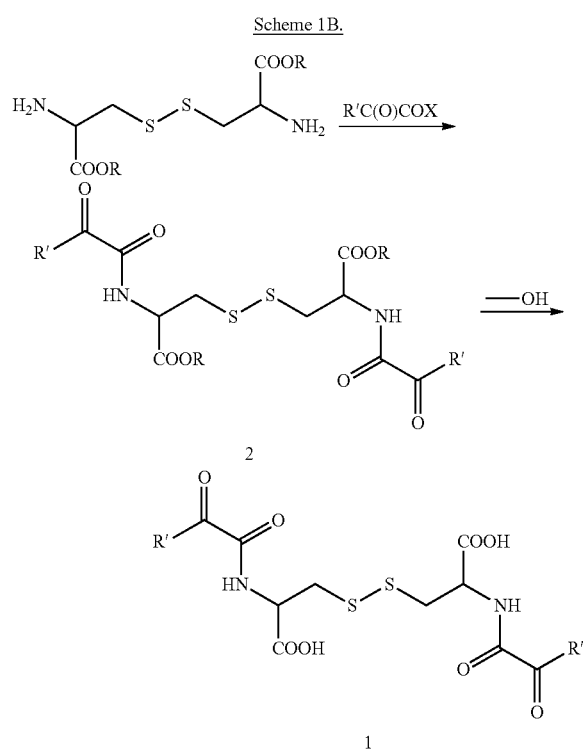

Scheme 1B.

As shown in Scheme 1A, an O-protected cysteine derivative, for example L-cysteine methyl ester or the like, may be S-protected, for example using trityl chloride or the like, zotriazole (DCC/HOBT) or the like, in a solvent such as DMF or THF or the like. Oxidative deprotection with concomitant disulfide formation is accomplished by treatment, for example, with iodine to give a protected cystine derivative. Hydrolysis of the ester groups, for example with aqueous sodium hydroxide in an alcoholic solvent, produces the target compound 1.

Alternatively, as shown in Scheme 1B, the order of these transformations may be altered. Beginning with an O-protected cystine derivative, for example L-cystine dimethyl ester, this material may be N-acylated with an aliphatic a-ketoacid, preferentially 2-oxovaleric acid, 2-oxo-4-methylvaleric acid, 2-oxo-3-methylvaleric acid or the like, in the presence of an activating agent such as WSC or DCC/HOBT or the like, in a solvent such as DMF or THF or the like. Hydrolysis of the ester groups, for example with aqueous sodium hydroxide in an alcoholic solvent, produces the target compound 1.

Intermediate esters of structure 2 may also serve as cystine prodrugs to deliver enhanced levels of cystine to the CNS. The strategy described above may also be employed to deliver enhanced levels of monomer cysteine, or of a corresponding prodrug, to the CNS. Thus, as described in Scheme 2, compounds 1 or 2 can be reductively cleaved, for example using a metal such as zinc or tin or the like in a solvent such as water or methanol or the like, in the presence of acid; or, using a reducing agent such as sodium borohydride or the like, in a solvent such as THF or ethanol or the like, to give target compounds 3 and 4. These compounds can then optionally be S-acylated, for example using an acid chloride such as acetyl chloride or an acid anhydride such as acetic anhydride or the like, in the presence of a base such as sodium hydroxide or sodium bicarbonate or the like, in a solvent such as water or ethanol or the like, to give target compounds 5 and 6.

Scheme 2.

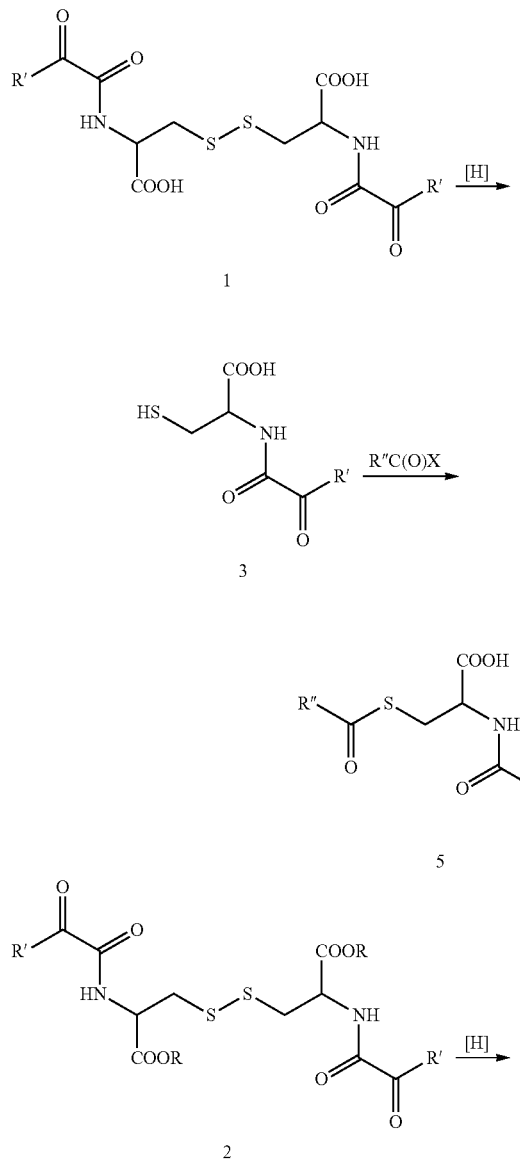

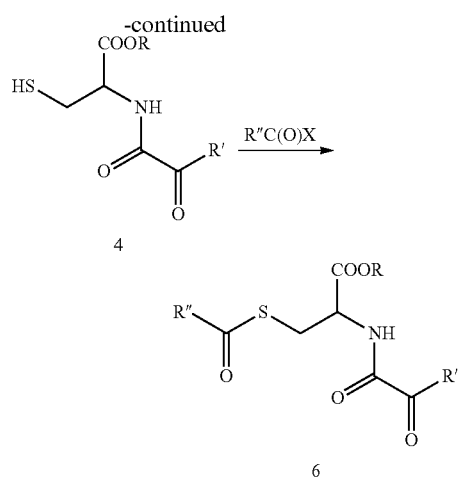

Certain esters, in particular esters of small aliphatic amino acids such as valine, also demonstrate enhanced uptake by virtue of interaction with the hPEPT1 transporter. As described in Scheme 3A, S-acylated cysteine derivatives, such as compound 7, can be prepared starting with an N-protected cystine derivative (such as diacetyl L-cystine, or di-N-Boc-L-cystine, or di-N-allyloxycarbonyl-L-cystine, or the like) by S-acylation with a suitably protected aliphatic amino acid such as Boc-L-valine or allyloxycarbonyl-L-leucine or the like, activated for example with DCC/HOBT or WSC/N-hydroxysuccinimide (WSC/NHS) or the like, optionally in the presence of a base such as triethylamine or sodium bicarbonate or the like, in a solvent such as water or ethanol, or THF, or DMF or the like.

Removal of the protecting group (PG), for example removal of tert-butyloxycarbonyl (Boc) using trifluoroacetic acid (TFA) or removal of allyloxycarbonyl (Alloc) using palladium or nickel or the like, provides compound 7. Removal of the orthogonal protecting group on the cysteine nitrogen as described above gives compound 8. Alternatively, the order of the removal of these protecting groups can be reversed to give compound 8 via a different route. Alternatively, both protecting groups can be the same, allowing for complete deprotection to arrive at compound 8 in a single step. In all cases it is important that products are isolated as ammonium salts to avoid the possibility of S→N acyl transfer.

Scheme 3A.

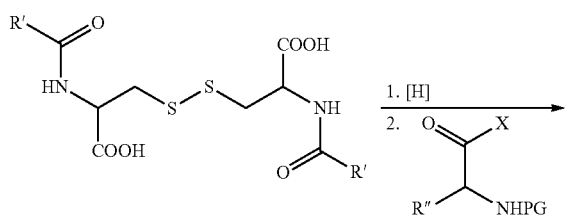

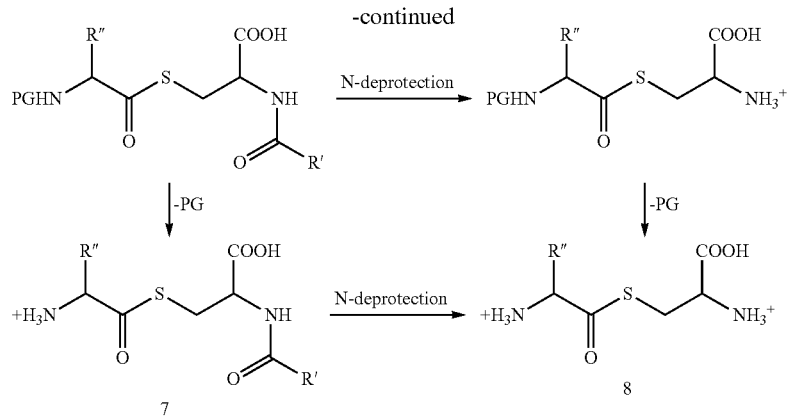

As demonstrated in Scheme 3B, ester prodrug forms of the S-aminoacyl derivatives 7 & 8 can also be prepared. All procedures are as described above, with the exception that the starting material is now an N-protected cystine ester such as di-N-Boc-L-cystine methyl ester or di-N-Alloc-L-cystine tert-butyl ester or the like. In an alternative strategy for the synthesis of compounds 7 and 8, compounds 9 and 10 may be converted via cleavage of a suitable ester group, for example removal of an allyl ester using palladium or nickel.

be S-aminoacylated to produce substrates for hPEPT1. N-acylation of L-cystine dimethyl ester with an N-protected, activated form of glycine such as Boc-glycine-NHS or the like gives the corresponding glycine amide. Removal of the N-protecting group under suitable conditions, for example removal of a Boc group with TFA, followed by optional warming of the product under basic conditions, for example after neutralization with sodium bicarbonate, gives the corresponding cystine bis-diketopiperazine 11a.

Scheme 3B.

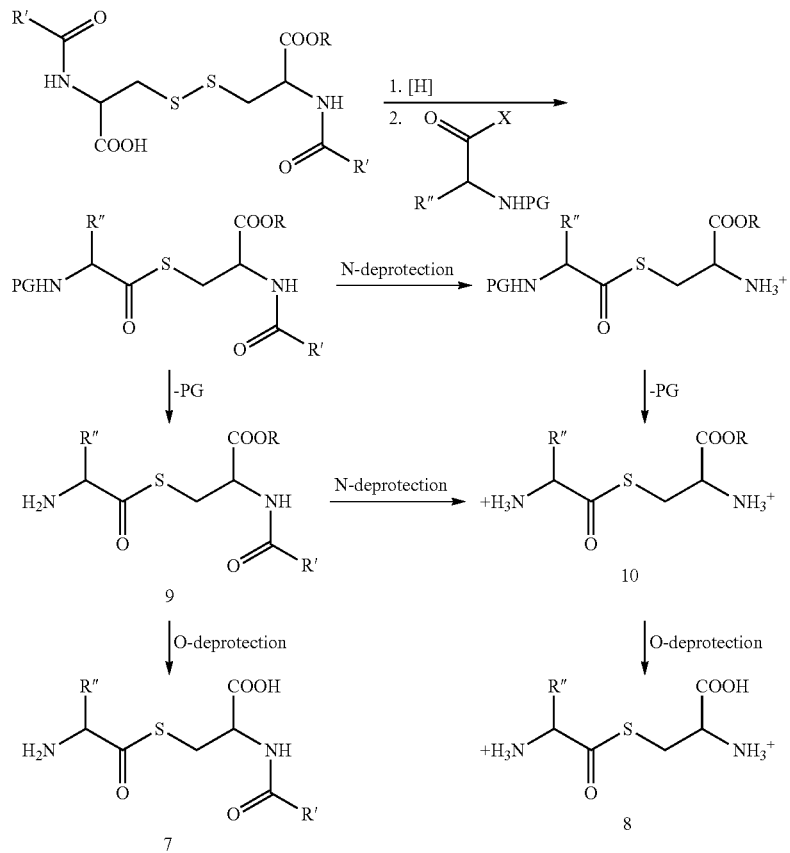

Scheme 3C demonstrates that alternative prodrug forms of cysteine, for example the cys-gly diketopiperazine, can also To prepare the corresponding cysteine S-acylated prodrug, 11a is reductively cleaved, for example using a metal such as zinc or tin or the like in a solvent like water or methanol or the like, in the presence of acid; or, using a reducing agent such as sodium borohydride or the like, in a solvent such as THF or ethanol or the like, and then S-acylated, for example using an acid chloride such as acetyl chloride or an acid anhydride like acetic anhydride or the like, in the presence of a base such as sodium hydroxide or sodium bicarbonate or the like, in a solvent such as water or ethanol or the like, to give target compound 11b.

sponding acyloxyalkyl carbamate. Oxidative deprotection of sulfur, for example using iodine in ethanol or the like, provides the corresponding disulfide 13. Removal of a suitably protected ester under mild conditions, for example of an allyl ester with palladium or nickel or removal of a p-methoxyphenyl ester with dilute acid, provides the corresponding diacid 12. Reductive cleavage of 12, for example using a metal such as zinc or tin or the like in a solvent such as water or methanol or the like, in the presence of acid; or, using a reducing agent

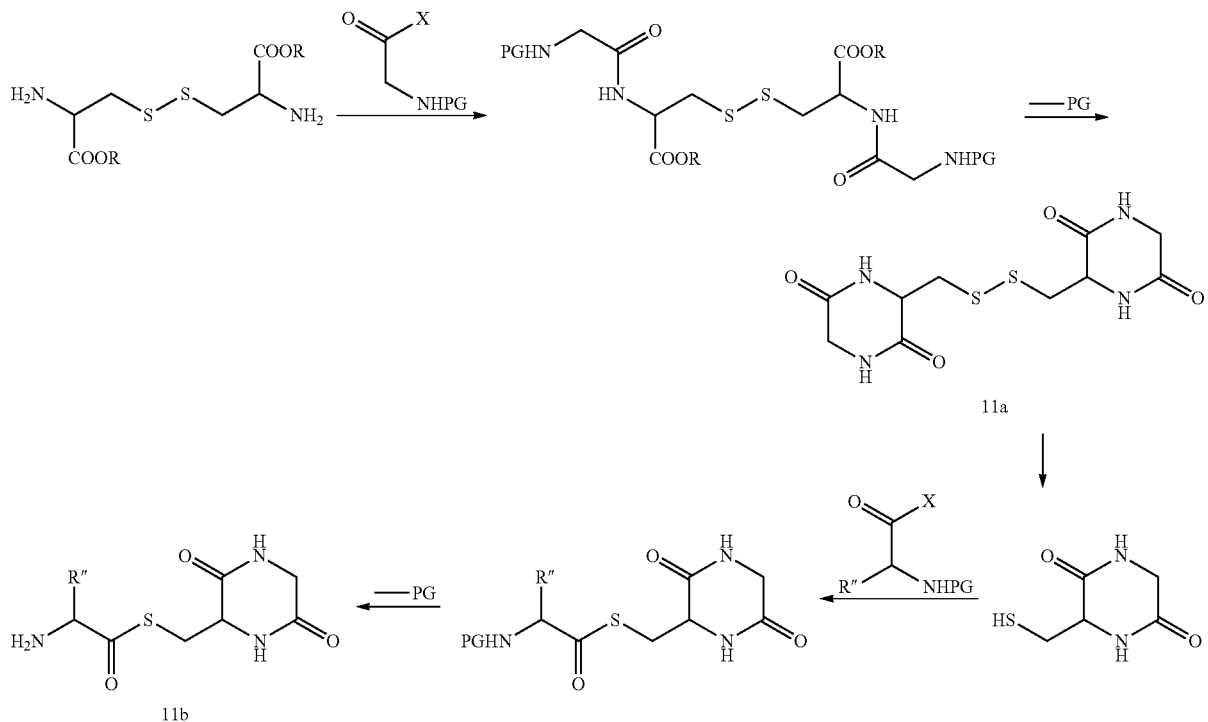

Scheme 3C.

Acyloxyalkyl Carbamate Prodrugs

Acyloxyalkyl carbamate prodrugs can improve drug uptake while undergoing ready in vivo conversion. The preparations of compounds 12, 13, 14 & 15 of this type are described in Scheme 4.

A suitably S-protected cysteine ester prepared as described in Scheme 1 is reacted with an activated acyloxy-alkoxycarbonate, for example acetoxyethyl-oxycarbonyl p-nitrophenyl carbonate or the like, in a solvent such as water or THF or DMF or the like, in the presence of a base such as sodium bicarbonate or triethylamine or the like, to give the correlike sodium borohydride or the like, in a solvent such as THF or ethanol of the like, produces a free thiol which can then be S-acylated, for example using an acid chloride such as acetyl chloride or an acid anhydride such as acetic anhydride or the like, in the presence of a base such as sodium hydroxide or sodium bicarbonate or the like, in a solvent such as water or ethanol or the like, to give target compound 14.

Alternatively, the order of O-deprotection and S-cleavage/acylation steps can be reversed, in which case the intermediate is compound 15.

Scheme 4.

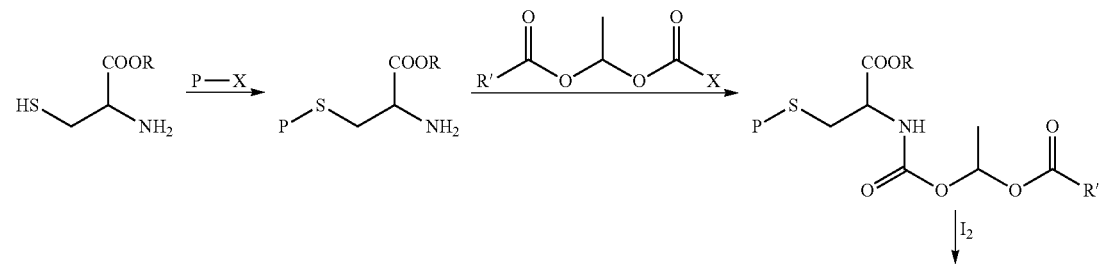

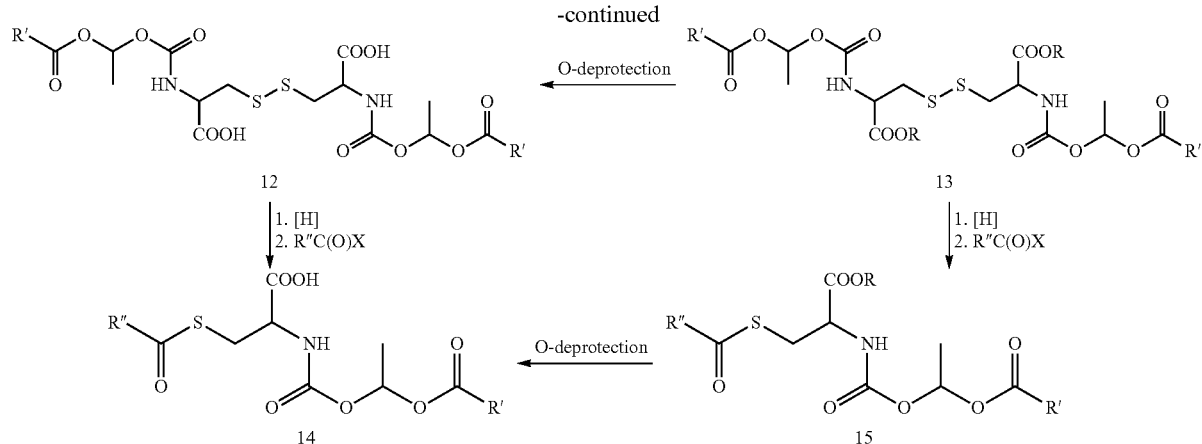

Nutrient Transporter Substrates

CNS levels of cysteine can also be increased through the use of compounds which take advantage of high-capacity nutrient transporters (in other words, utilizing amino acid and/or sugar transport systems). For example, L-tyrosyl esters of cysteine or cystine like 16, 17, 18 or 19 may be prepared as described in Scheme 5, as follows.

Di-N-protected cystine, for example di-N-Boc-L-cystine or the like, is activated, for example with DCC/HOBT or WSC/NHS or the like, and coupled with suitably protected L-tyrosine, for example N-Boc-L-tyrosine-methyl ester or the like. Removal of the protecting groups on tyrosine provides 16. Compound 16 may optionally be further processed by removal of the compatible, orthogonal N-protecting group on the cysteine moiety (for example, removal of a Boc group with TFA or an Alloc group with palladium or nickel) to give product 18.

To make the corresponding S-acylcysteine derivatives, the tyrosine coupling product is reductively cleaved, for example using a metal such as zinc or tin or the like in a solvent such as water or methanol or the like, in the presence of acid; or, using a reducing agent such as sodium borohydride or the like, in a solvent such as THF or ethanol or the like, and then S-acylated, for example using an acid chloride such as acetyl chloride or an acid anhydride such as acetic anhydride or the like, in the presence of a base such as sodium hydroxide or sodium bicarbonate or the like, in a solvent such as water or ethanol or the like. Removal of the protecting groups on tyrosine gives the target compound 17. Compound 17 may optionally be further processed by removal of the compatible, orthogonal N-protecting group on the cysteine moiety (for example, removal of a Boc group with TFA or an Alloc group with palladium or nickel) to give product 19.

Scheme 5.

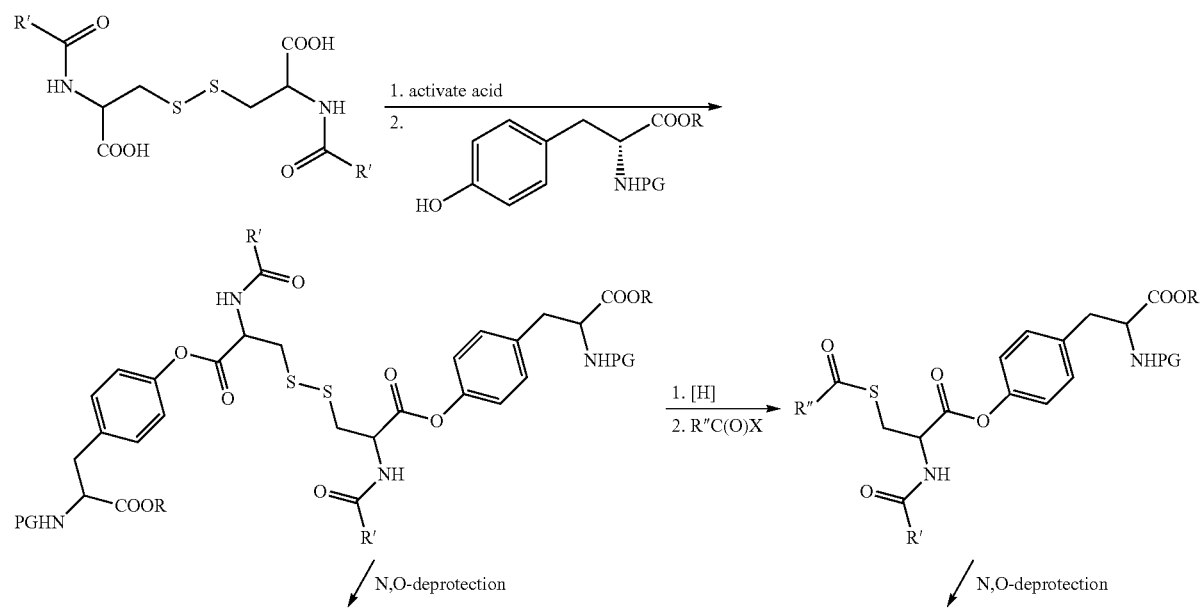

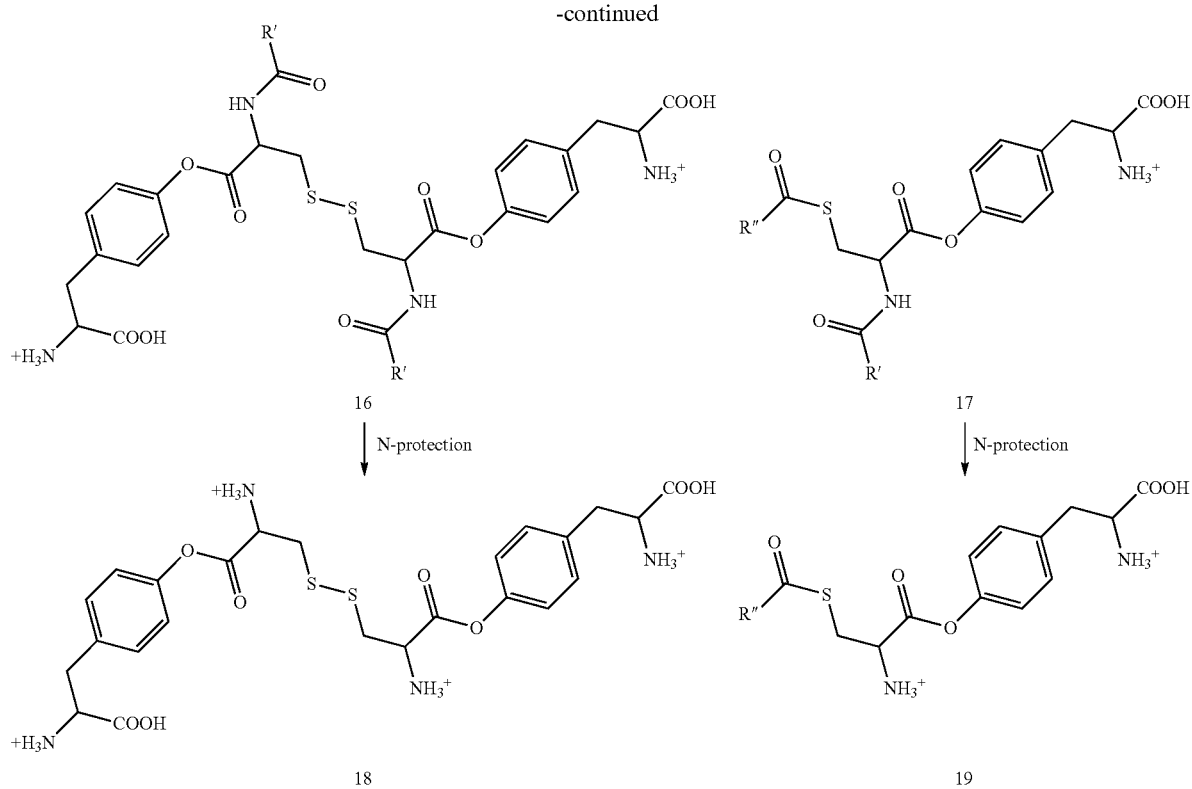

Cysteine/cystine levels in the brain can also be raised through treatment with prodrugs that are actively imported into brain via the dihydropyridine/pyridinium redox transporter.

Prodrugs such as compounds 20, 21, 22, and 23 can be prepared according to the procedures in Scheme 6. Thus, N-methyldihydronicotinic acid, prepared from methyl nicotinate via reaction of the pyridine nitrogen with methyl iodide in a solvent such as methanol or the like, followed by reduction of the resultant pyridinium salt with sodium dithionite in a solvent such as water and hydrolysis of the ester group using aqueous sodium hydroxide or the like, is coupled with a cystine ester such as L-cystine dimethyl ester with activating agent like DCC, in a solvent such as THF or pyridine or the like to give amide 21.

Hydrolysis of the ester groups of compound 21, for example with aqueous sodium hydroxide, gives the diacid 20.

Optionally the disulfide bond of compound 20 can be cleaved, for example using a metal such as zinc or tin or the like in a solvent such as water or methanol or the like, in the presence of acid; or, using a reducing agent like sodium borohydride or the like, in a solvent like THF or ethanol or the like, and then S-acylated, for example using an acid chloride such as acetyl chloride or an acid anhydride such as acetic anhydride or the like, in the presence of a base such as sodium hydroxide or sodium bicarbonate or the like, in a solvent such as water or ethanol or the like, to give target compound 22.

Alternatively, the order of ester hydrolysis and disulfide reduction/acylation can be reversed, in which case the intermediate is compound 23. It is important that oxygen is excluded from reactions involving substrates that contain the dihydropyridine group.

Scheme 6.

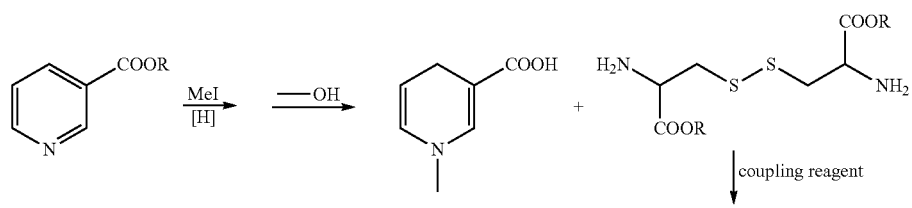

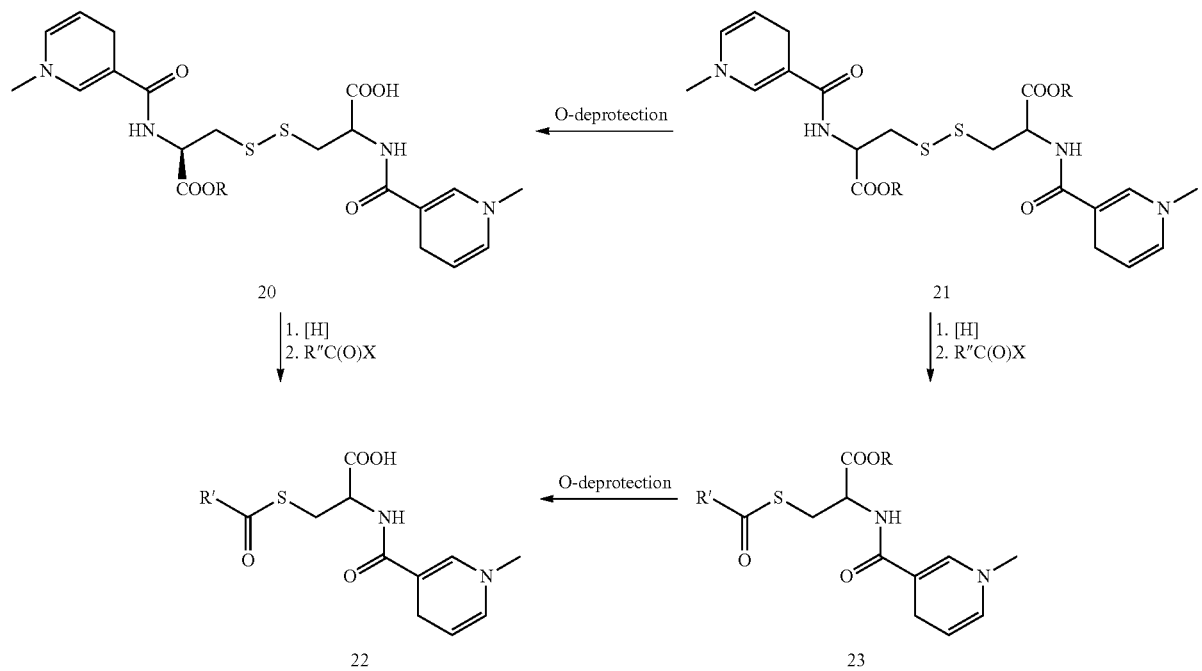

Glucose transporters like GLUT-1 can also be used to increase drug levels in the brain. Compounds such as 24, 25, 26, and 27 can be prepared as exemplified in Scheme 7, which describes a prodrug linked to C-6 of glucose.

Similar procedures, employing alternatively protected glucose derivatives as starting materials, can be employed to prepare prodrugs linked at other sites on the glucose carrier. A suitably N-protected cystine derivative, for example di-N-Boc-L-cystine, is activated, for example using DCC/HOBT or WSC/NHS or the like, and coupled with a suitably protected glucose derivative, for example tetra-O-acetyl-D-glucose or the like, optionally in the presence of an acylation catalyst such as 4-dimethylaminopyridine (DMAP). Removal of the protecting groups on glucose, for example by hydrolysis of O-acetyl groups using aqueous sodium hydroxide in a solvent such as ethanol, gives the target compound 24, which optionally may be N-deprotected, for example by removal of Boc-groups using TFA, to give the target compound 26.

Alternatively the disulfide bond of compound 24 can be cleaved, for example using a metal such as zinc or tin or the like in a solvent such as water or methanol or the like, in the presence of acid; or, using a reducing agent like sodium borohydride or the like, in a solvent such as THF or ethanol or the like, and then S-acylated, for example using an acid chloride such as acetyl chloride or an acid anhydride such as acetic anhydride or the like, in the presence of a base such as sodium hydroxide or sodium bicarbonate or the like, in a solvent such as water or ethanol or the like, to give target compound 25. N-deprotection of 25, for example by removal of Boc-groups using TFA, gives target compound 27.

Alternatively, an appropriate protecting group can be retained as a prodrug on the sugar hydroxyls. For example in the above-described procedures, when PG is acetyl, the first protecting-group step can be eliminated, resulting in analogs of 24, 25, 26, and 27 in which the hydroxyl groups on glucose are O-acetylated.

Scheme 7.

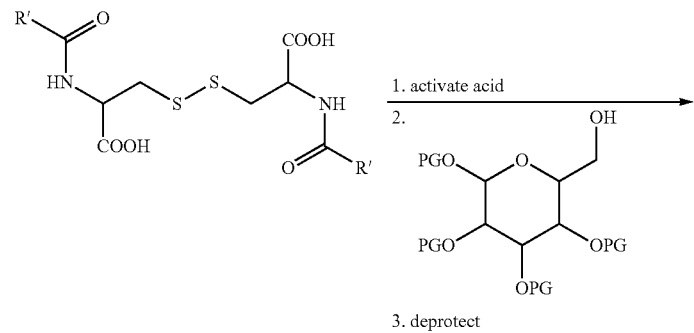

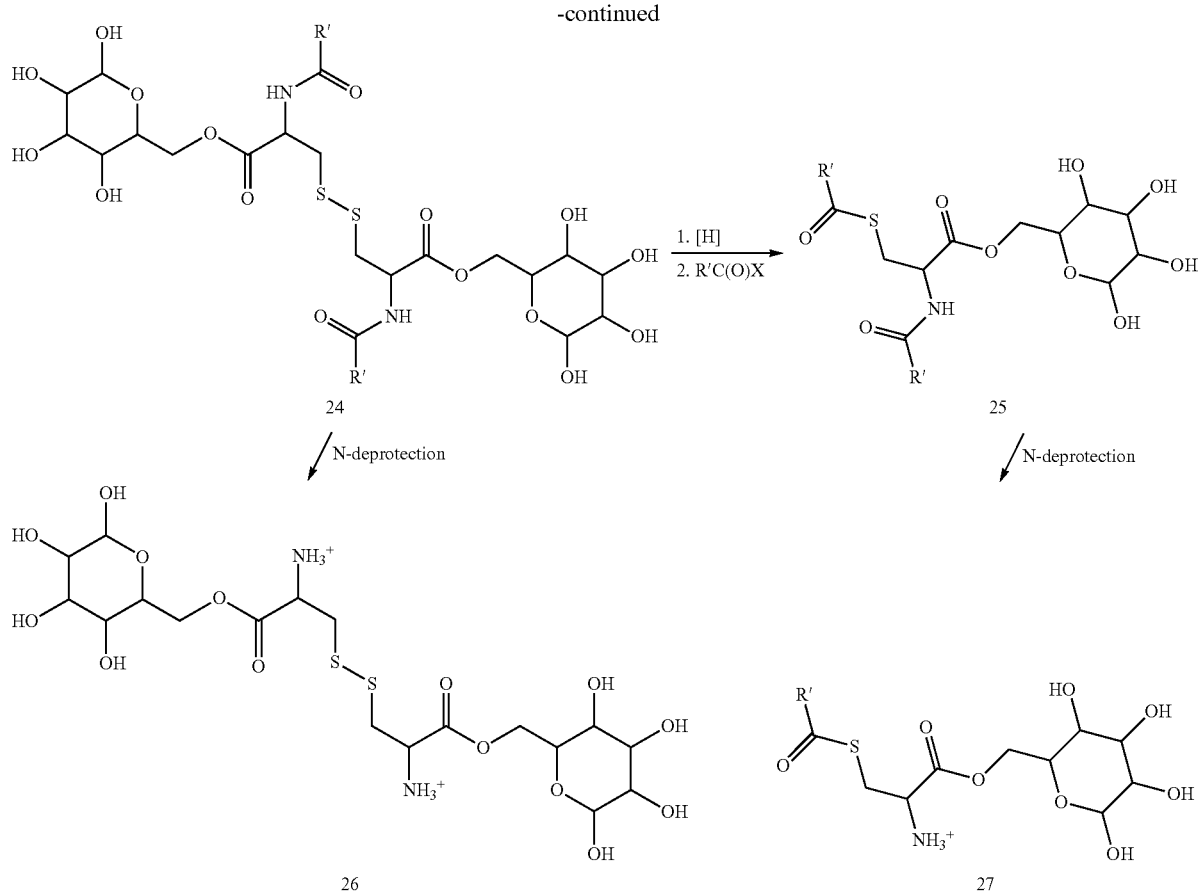

24 25 26 27

Alternatively, the glucose carrier molecule may be attached to the amine group of cysteine/cystine via a carbamate linkage, as shown in Scheme 8. Thus, a suitably protected glucose derivative is converted to an activated carbonate, for example by treatment with carbonyl-diimidazole (CDI) or triphosgene or the like, in a solvent such as THF or DMF or the like, and then reacted with a cystine ester such as L-cystine methyl ester or the like.

The resultant product 28 may be O-deprotected, for example with aqueous sodium hydroxide in a solvent such as methanol or ethanol or the like, to give the corresponding diacid 30. Reductive cleavage of compound 30, for example using a metal such as zinc or tin or the like in a solvent such as water or methanol or the like, in the presence of acid; or, using a reducing agent like sodium borohydride or the like, in a solvent such as THF or ethanol of the like, produces a free thiol which can then be S-acylated, for example using an acid chloride such as acetyl chloride or an acid anhydride such as acetic anhydride or the like, in the presence of a base such as sodium hydroxide or sodium bicarbonate or the like, in a solvent such as water or ethanol or the like, to give target compound 31.

Alternatively, the order of O-deprotection and S-cleavage/acylation steps can be reversed, in which case the intermediate is compound 29.

Scheme 8.

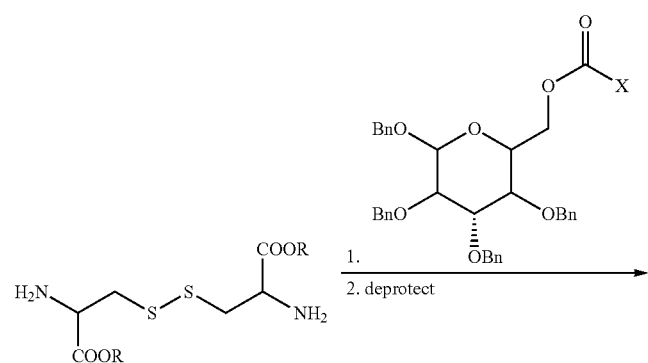

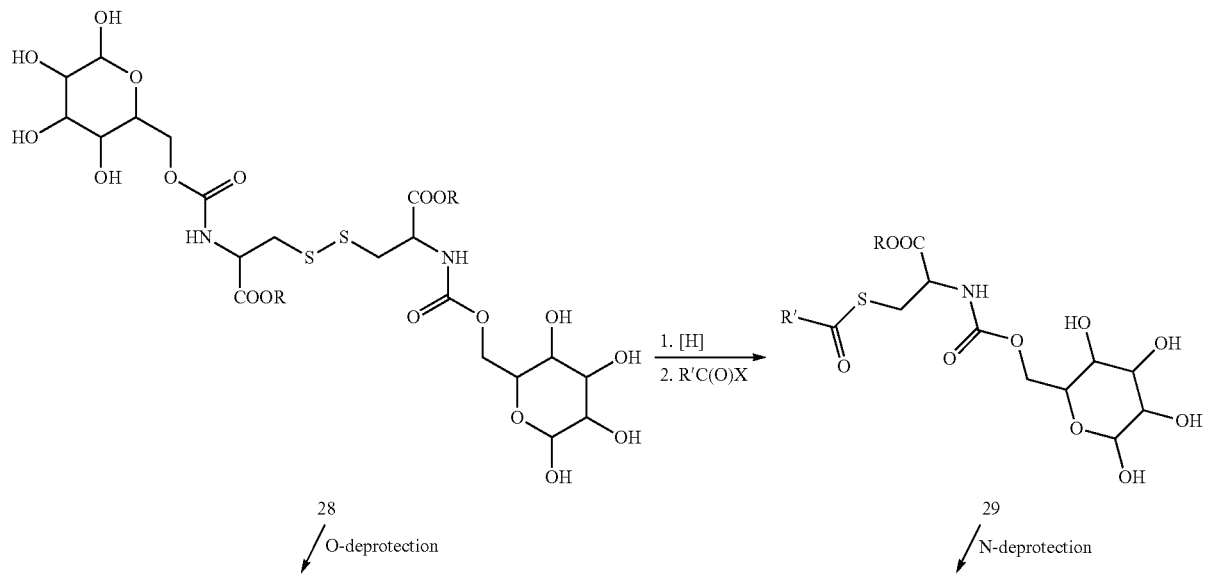

28 → 29

O-deprotection ↓

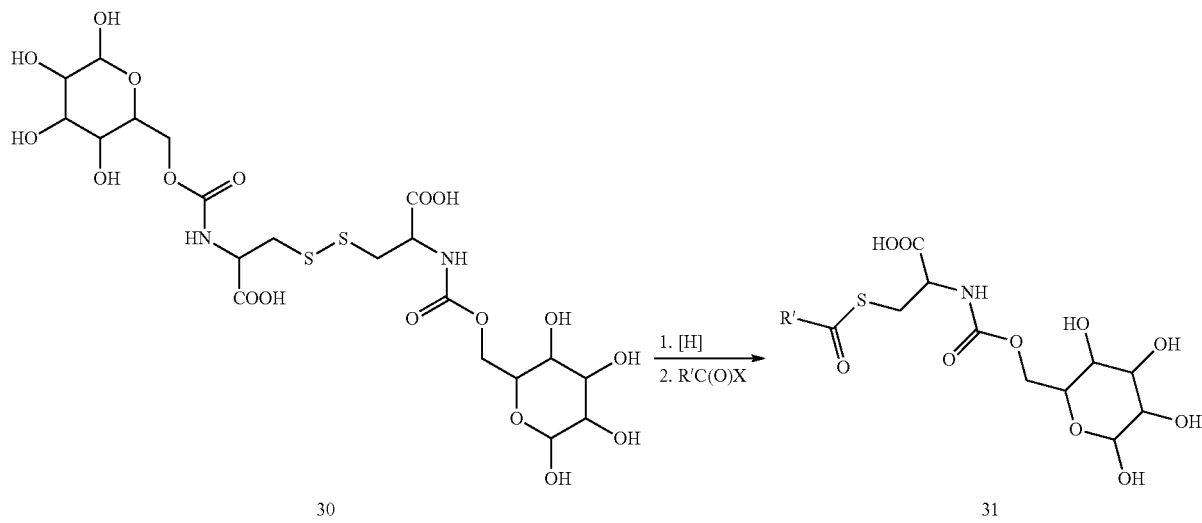

30 → 31

Additionally, thiazolidine formation can be used as an alternative approach to linking cysteine (though not cystine) to a carbohydrate carrier. Compounds such as 32 and 33 may be prepared as described in Scheme 9 below. Combining L-cysteine or a protected form such as L-cysteine methyl ester or the like, with glucose, in the presence of an acid catalyst such as aqueous HCl or para-toluenesulfonic acid (p-TsOH) or camphorsulfonic acid (CSA) or the like, in a solvent such as ethanol or the like, provides the desired derivative 32 or 33.

Alternatively, ester 32 can be hydrolyzed, for example using a base such as sodium hydroxide or the like in a solvent such as ethanol or methanol or water, or a solvent mixture including these, or the like, to give thiazolidine acid 33.

Scheme 9.

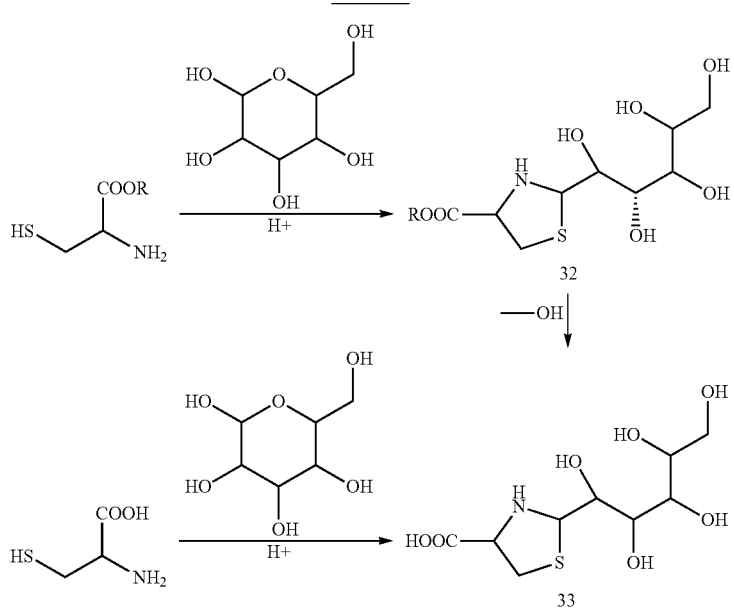

Other Prodrugs

Cyclic carbamate prodrugs such as 34 and 35 can also increase systemic levels of cystine. Representative compounds can be prepared according to the protocols described in Scheme 10. Treatment of cystine with an activated carbonate such as CDI or triphosgene or p-nitrophenyl chloroformate or the like, in a solvent such as THF or DMF or the like, provides the cyclic carbamate 34. Compound 34 may optionally be N-acylated with an activated acid such as acetyl chloride or acetic anhydride or the like, in the presence of a base such as triethylamine or pyridine or the like, and optionally in the presence of an acylation catalyst such as DMAP or the like, to give compound 35.

Haloalkyl thioesters have also been shown to act as prodrugs to improve absorption while converting efficiently to parent drug in vivo. Compounds 36 and 37 can be prepared using the procedures described in Scheme 11.

Cystine prodrug 36 can be prepared starting with S-protected, N-acyl cysteine derivative being activated with CDI or the like and reacted with a thiol-delivering reagent such as sodium hydrosulfite or the like, in a solvent such as water or THF or the like, or a mixture of these solvents.

The intermediate thiolacid is S-alkylated, for example with bromofluoromethane or chlorofluoromethane or the like, in a solvent such as THF or methanol or water or the like, optionally in the presence of an activating agent such as sodium iodide. The resultant thiolester is oxidatively deprotected to give compound 36. The corresponding cysteine analog 37 is prepared from an N-acyl, S-acyl cysteine derivative via an activation/thiolation/alkylation strategy similar to that described above.

Scheme 10.

Scheme 11.

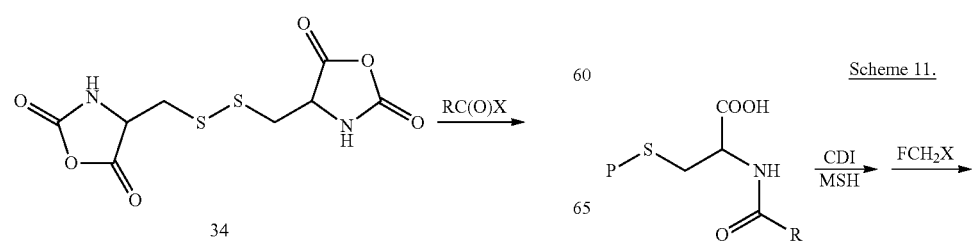

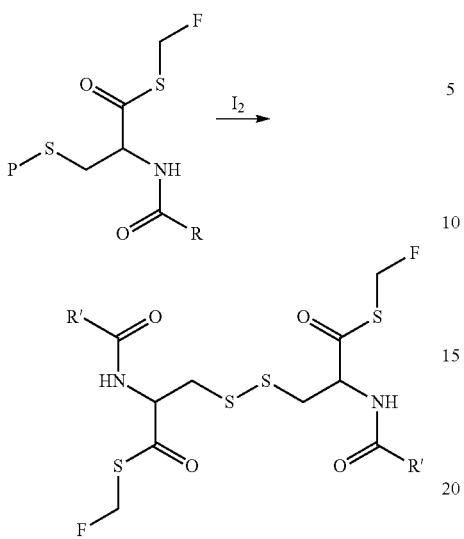

What is claimed is:

1. A compound of formula I:

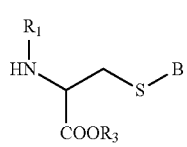

where
B is selected from the group consisting of:

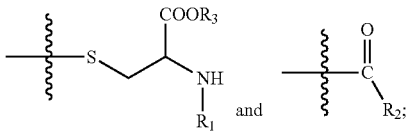

and $R_1$ is

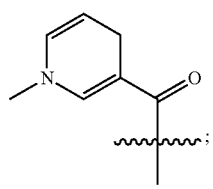 [SMILES: *C(=O)C1=CN(C)C=CC1]

$R_2$ is a linear or branched $C_1$-$C_6$ alkyl;
$R_3$ is H;
or a pharmaceutically acceptable salt thereof.

2. The compound of claim 1, where B is

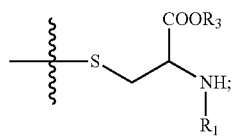

3. The compound of claim 1, where B is

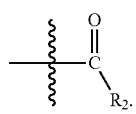

4. A pharmaceutical composition comprising the compound of claim 1 and a pharmaceutically acceptable carrier.

5. A method of treating schizophrenia comprising administering to a subject in need thereof a therapeutically effective amount of the compound of claim 1.

* * * * *